United States Patent [19]

Hurel

[11] Patent Number: 5,650,395
[45] Date of Patent: Jul. 22, 1997

[54] TREATMENT OF PULMONARY HYPERTENSION

[76] Inventor: Steven Hurel, Cruachan, Mt. Isaac, St. Lawrence, Jersey, Channel Islands

[21] Appl. No.: 403,280

[22] Filed: Mar. 13, 1995

[51] Int. Cl.$^6$ .......................... C07K 14/555; A61K 38/16
[52] U.S. Cl. .......................... 514/16; 530/324; 530/325; 530/326; 530/328; 530/309
[58] Field of Search .......................... 514/16; 530/328, 530/309, 324, 325, 326

[56] References Cited

U.S. PATENT DOCUMENTS

| | | | |
|---|---|---|---|
| 5,084,555 | 1/1992 | Coy et al. | 530/328 |
| 5,244,883 | 9/1993 | Cai et al. | 514/15 |
| 5,369,094 | 11/1994 | Schally et al. | 514/15 |
| 5,428,019 | 6/1995 | Edwards et al. | 514/16 |

OTHER PUBLICATIONS

Gosney et al., "Pulmonary Endocrine Cells in Pulmonary Arterial Disease", Arch Pathol Lab Med 113:337–341, Apr. 1989.

Heath et al., "Pulmonary Blood Vessels and Endocrine Cells in Subacute Infantile Mountain Sickness", Respiratory Medicine 83:77–81, 1989.

Kulik et al., "Pulmonary Vascular Effects of Bombesin and Gastrin–Releasing Peptide in Conscious Newborn Lambs", J. Appl. Physiol. Resp. Env. Exe. Phys. 55:1093–1097, 1983.

Obara et al., "The Effects of Various Peptides on the Isolated Pulmonary Artery", Peptides 10:241–243, 1989.

Heath et al., "Pulmonary Endocrine Cells in Hypertensive Pulmonary Vascular Disease", Histopathology 16:21–28 1990.

*Primary Examiner*—Cecilia J. Tsang
*Assistant Examiner*—Lynn Touzeau
*Attorney, Agent, or Firm*—Fish & Richardson P.C.

[57] ABSTRACT

A method of lowering the pulmonary blood pressure of a subject suffering from pulmonary hypertension. The method includes administering to the subject an effective amount of a bombesin antagonist.

22 Claims, 1 Drawing Sheet

TREATMENT OF PULMONARY HYPERTENSION

FIELD OF THE INVENTION

This invention relates to a method of lowering the pulmonary blood pressure of a subject suffering from pulmonary hypertension.

BACKGROUND OF THE INVENTION

Pulmonary circulation is one of low resistance, about one-eighth of systemic blood pressure. Pulmonary hypertension is caused largely by an increase in pulmonary vascular resistance and is classified clinically as either primary or secondary. Secondary pulmonary hypertension, the more common form, is generally a result of (1) chronic obstructive or interstitial lung disease; (2) recurrent pulmonary emboli; (3) liver disease; or (4) antecedent heart disease. Primary pulmonary hypertension is diagnosed only after all known causes of increased pulmonary pressure are excluded.

Plexogenic pulmonary hypertension is a histological definition identified by the presence of plexiform lesions, concentric luminal proliferation, and fibrinoid necrosis within the pulmonary vasculature. These lesions are characteristic of primary pulmonary hypertension and secondary pulmonary hypertension, e.g., associated with congenital cyanotic heart disease and hepatic cirrhosis.

Untreated pulmonary hypertension leads to progressive cor pulmonale with right ventricular hypertrophy and strain, and subsequently a pulmonary crisis develops with decompensated right heart failure. The prognosis for patients with pulmonary hypertension is poor, with a median survival time of 2.3 years from diagnosis.

Within the lungs exists an autonomous endocrine system, termed the pulmonary neuroendocrine system (PNES). This system has been shown to secrete the humoral peptides calcitonin and bombesin-like peptide, e.g., gastrin related peptide (GRP). However, neither bombesin nor GRP, under a wide range of experimental conditions, have any demonstrable in vivo pulmonary haemodynamic effect. Additionally, bombesin was shown not to have an effect on isolated pulmonary arteries. Furthermore, it has not been reported that a bombesin antagonist is capable of lowering the pulmonary blood pressure of a patient.

SUMMARY OF THE INVENTION

The present invention relates to a method for lowering the pulmonary blood pressure (i.e., systolic or diastolic) of a subject (i.e., a mammal such as a human) suffering from pulmonary hypertension, e.g., either primary or secondary pulmonary hypertension.

The method of this invention includes the step of administering to the subject an amount of a bombesin antagonist which is therapeutically effective to lower the pulmonary blood pressure of the subject. The administration can be effected enterally or parenterally, e.g., intravenously, subcutaneously, transdermally, or by implantation of a sustained release formulation, and by inhalation (such as aerosol delivery). Preferably, the bombesin antagonist is administered to the subject continuously, e.g., via intravenous administration using an infusion pump or via subcutaneous implantation of a sustained release formulation.

Also within the scope of this invention is the use of a bombesin antagonist for the manufacture of a medicament for lowering the pulmonary systolic or diastolic pressure.

A therapeutically effective amount of a bombesin antagonist to be administered to a subject depends upon the condition being treated, the route of chosen administration, and the specific activity of the chosen bombesin antagonist, and ultimately will be determined by the attending physician or veterinarian.

The bombesin antagonist can be administered either before or during pulmonary crises. Further, it can also be administered prior to single-lung, double-lung, or heart-lung transplant. In addition, it is sometimes desirable to give the bombesin antagonist to the subject over a long period as an adjunct to the standard therapies for heart failure as a result of pulmonary hypertension, e.g., chronic obstructive lung disease.

The bombesin antagonist may be administered either alone or in combination with other agents. Examples of such agents include, but are not limited to, vasodilators (e.g., adenosine, β-adrenergic agonists or antagonists, α-adrenergic blockers, diuretics, smooth muscle vasodilators, nitrates, and angiotensin-converting enzyme inhibitors), calcium channel antagonists (e.g., nifedipine or diltiazem), prostacycline, anticoagulants, nitroprusside, hydralazine, nitrous oxide, L-arginine, and digoxin. The co-administration of these agents can be performed before, after, or during the administration of the bombesin antagonist.

While it is possible for the bombesin antagonist to be administered as a pure or substantially pure compound, it is preferable to present it as a pharmaceutical formulation. Formulations to be used in the present invention, for both humans and animals, can include a bombesin antagonist, and one or more pharmaceutically acceptable carriers therefor. Optionally, other therapeutic ingredients can also be included.

The carrier must be "acceptable" in the sense of being compatible with the active ingredient(s) of the formulation, unharmful to the subject to be treated, and, preferably, capable of stabilizing peptides. Desirably, the formulation should not include oxidizing agents or other substances with which peptides are known to be incompatible. On the other hand, highly oxidative conditions can lead to the formation of cysteine sulfoxide and to the oxidation of tryptophane. Consequently, it is important to carefully select the excipient.

The formulations may conveniently be presented in unit dosage form and may be prepared by any of the methods well known in the art of pharmacy. All methods include the step of bringing the active ingredient(s) into association with the carrier which constitutes one or more accessory ingredients.

Formulations suitable for intravenous administration, on the other hand, conveniently comprise sterile aqueous solutions of the active ingredient(s). Preferably, the solutions are isotonic with the blood of the subject to be treated. Such formulations may be conveniently prepared by dissolving solid active ingredient(s) in water to produce an aqueous solution, and rendering the solution sterile. The formulation may be presented in unit or multi-dose containers, for example, sealed ampoules or vials.

Other features and advantages of the invention will be apparent from the following drawing and detailed description of embodiments thereof, as well as from the claims.

BRIEF DESCRIPTION OF THE DRAWING

The drawing is first described.

DETAILED DESCRIPTION OF THE INVENTION

Figure 1:
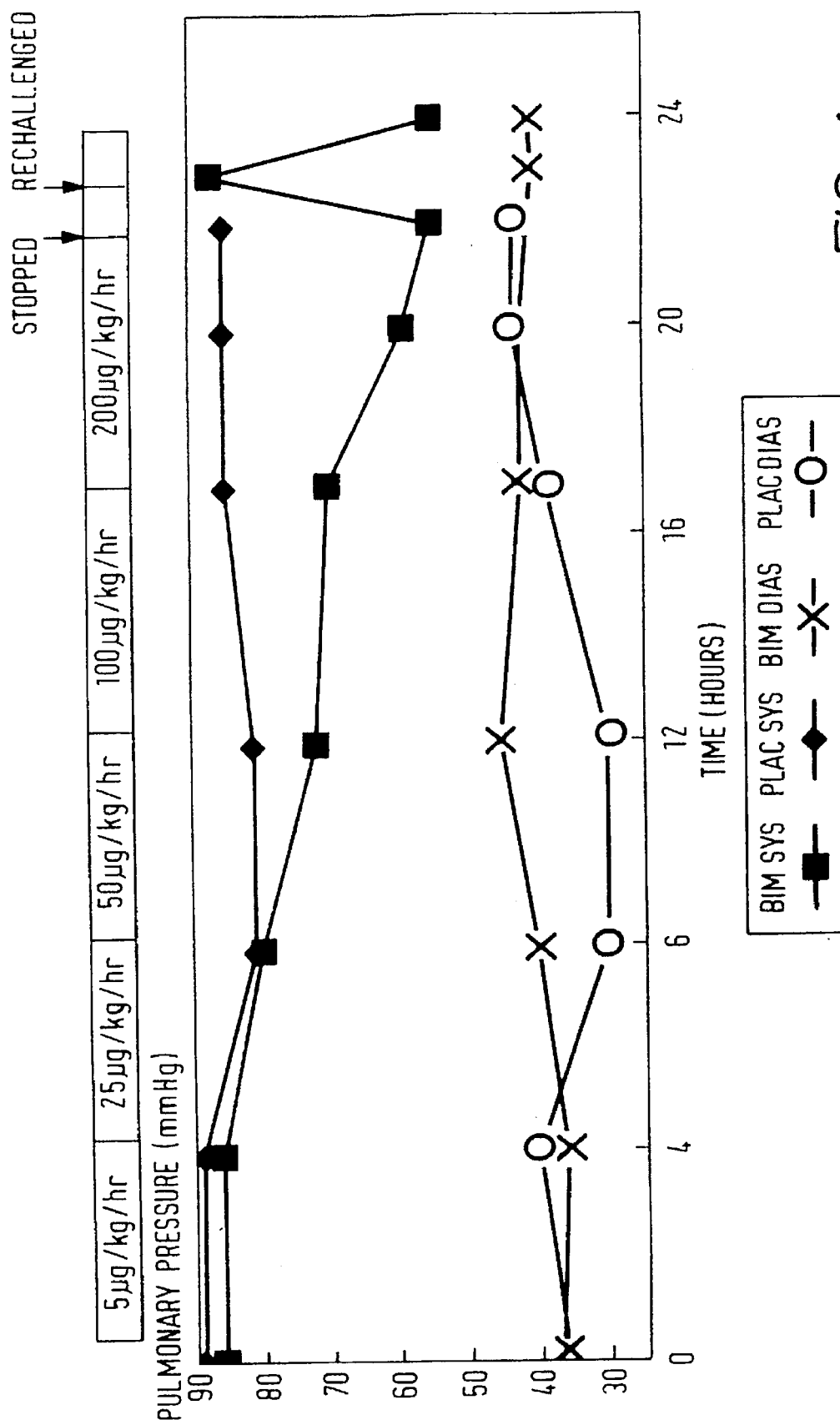
FIG. 1 is a graph comparing the effect of BIM-26226, a bombesin antagonist, and a saline placebo on pulmonary pressure.

The following specific embodiments are to be construed as merely illustrative, and not limitative of the remainder of this disclosure in any way whatsoever. Furthermore, all of the publications recited in this disclosure are hereby incorporated by reference. It is believed that one of ordinary skill in the art can, based on the description herein, utilize the present invention to its fullest extent.

Bombesin Antagonists

Bombesin, a tetradecapeptide, was first isolated from the skin of the frog Bombina bombina. Bombesin exhibits various biological activities in mammals, including stimulation of hormone secretion, smooth muscle contraction, splanchria vasodilation, and alteration of body temperature. See, e.g., Lagente, V., et al., Life Sciences, S3: PL75 (1993).

GRP is a 27-amino acid peptide first isolated from the porcine gut. The C-terminal amino acid sequence of GRP is almost identical to that of bombesin. Neuromedin C is a decapeptide that structure is identical to the last ten amino acids in the C-terminal region of GRP. Both GRP and neuromedin C possess bombesin-like properties, and are therefore known as bombesin-like peptides. Other bombesin-like peptides include litorin and neuromedin B.

Numerous structural analogs of bombesin-like peptides have been prepared which negate the biological activity of endogenous bombesin-like peptides. Such analogs are called bombesin antagonists herein.

Many existing bombesin antagonists have modifications from the natural peptide at the C-terminus, e.g., residue deletion or pseudopeptide bond between residues. Bombesin antagonists which can be used to practice the therapeutic method of the present invention include, but are not limited to, those covered by formulas or those specifically recited in the publications set forth below:

U.S. Pat. No. 4,207,311 (1980);
PCT Patent Application WO 89/02897 (1989);
European Patent Application 313158 A2 (1989);
European Patent Application 315367 A2 (1989);
European Patent Application 345990 A2 (1989);
PCT Patent Application WO 90/01037 (1990);
PCT Patent Application WO 90/03980 (1990);
U.S. Pat. No. 4,943,561 (1990);
Great Britain Patent Application 2237051A (1990);
PCT Patent Application WO 91/02746 (1991);
U.S. Pat. No. 5,068,222 (1991);
European Patent Application 434979 A1 (1991);
PCT Patent Application WO 92/02545 (1992);
PCT Patent Application WO 92/20707 (1992);
U.S. Pat. No. 5,084,555 (1992);
U.S. Pat. No. 5,244,883 (1993); and
PCT Patent Application WO 94/21674 (1994).

An example of bombesin antagonists which can be used to practice the method of this invention is the octapeptide BIM-26226. BIM-26226 is of the formula: H-D-$F_5$-Phe-Gln-TrP-Ala-Val-D-Ala-His-Leu-O-$CH_3$, in which each amino acid residue has the structure of —NH—C(R)H—CO— where R is the side chain, and the optically active residue is in the L-configuration unless the D-configuration is expressly designated. Note that D-$F_5$-Phe is an abbreviation of D-pentafluorophenylalanine.

Synthesis of Bombesin Antagonists

The synthesis of bombesin antagonists is exemplified by the description of how to prepare BIM-26226 as set forth below:

A 5-liter solid phase reaction vessel of a peptide synthesizer (Vega Biotechnologies, Model #2961, Tucson, Ariz.) was charged with 244.7 g of t-butyloxycarbonyl (Boc)-L-Leu Meisifield Resin, with a substitution of 0.75 mmoles/g. The peptide synthesizer was programmed to perform the following reaction cycle: (a) washing with methylene chloride; (b) deblocking twice with 20 percent trifluoroacetic acid in methylene chloride (1×2 min; 1×25 min); (c) washing with methylene chloride; (d) washing with isoproponal; (e) washing with methylene chloride; (f) neutralizing with 10% triethylamine in methylene chloride; and (g) washing with methylene chloride.

The neutralized resin was stirred with Boc-N-imidazole (tosyl) L-His and diisopropyl carbodimine in methylene chloride for 1 hr. The resin is washed once with dimethylformide (DMF) and three times with methylene chloride. The resin is then checked by the Kaiser ninhydrin test.

The following amino acids are then coupled successively by following steps (a) through (g) in the above wash program: Boc-D-Ala, Boc-L-Val, Boc-L-Ala, and Boc-L-Trp. These amino acids are coupled as preformed symmetrical anhydrides. The tosyl group is removed from the His residue before proceeding to the next coupling by washing the resin twice with a solution of hydroxybenzotriazole (HOBT)/DMF (40.6 g HOBT $H_2O$ in 2.5 l of DMF for one hour). The resin was then washed once with DMF and three times with methylene chloride. The above wash program was then followed, and Boc-L-Gln, preformed as an HOBT ester, was coupled. The above wash program was again followed and D-$F_5$-Phe was coupled as a preformed HOBT ester and then recoupled as a preformed symmetrical anhydride. The Boc group was then removed from the D-$F_5$-Phe residue, and the resin was dried to yield 345.9 g of peptide-resin.

The peptide was cleaved from the resin by reacting 345.9 g of peptide resin, 1.05 l of DMF, 1.75 l of methanol, and 0.70 l of triethylamine, at 40° C. for 19 hrs. The above cleavage procedure was then repeated to give additional peptide product. The product was purified by reverse phase HPLC and lyophilized to yield 30.9 g of peptide.

Other bombesin antagonists which can be used to practice the invention can be prepared by making appropriate modifications within the ability of someone of ordinary skill in this field.

Determining the Affinity of a Peptide for GRP Receptor

Below is a working example showing how one can screen for bombesin antagonists which have high affinity for GRP receptor.

Membranes for the GRP receptor binding assay were obtained by homogenizing cultured AR42J cells (ATCC No. CRL-1492; American Type Culture Collection, Rockville, Md.) using a Polytron homogenizer (Brinkman Instruments, Westchester, N.Y.) at a setting of 6 for 15 sec. in an ice-cold 50 mM Tris-HCl buffer (Buffer A; Sigma, St. Louis, Mo.). See Singh, et al., 258 Am. J. Physiol. G803 (1990). The homogenate was centrifuged twice at 39,000×g (10 min.) with an intermediate resuspension in fresh Buffer A. The final pellets were resuspended in Buffer A containing 0.1 mg/ml bacitracin and 0.1% bovine serum albumin (Buffer B) and held on ice for the receptor binding assay. Both bacitracin and bovine serum albumin were purchased from Sigma, St. Louis, Mo. Aliquots (0.4 ml) of the cell suspension were incubated with 0.05 ml of [$^{125}$I-Tyr$^4$] bombesin (~2200 Ci/mmol; New England Nuclear, Boston, Mass.) in Buffer B and 0.05 ml of the test peptide (e.g., BIM-26226) at various concentrations (e.g., 0M to $10^{-6}$M) in Buffer B. After a 30 min. incubation at 4° C., the bound [$^{125}$I-Tyr$^4$]

bombesin was separated from the free [$^{125}$I-Tyr$^4$]bombesin by rapid filtration through GF/B filters (Biomedical Research & Development, Gaithersberg, Md.) which had been previously soaked in 0.3% polyethyleneimine (Sigma, St. Louis, Mo.). The filters were then washed three times with 5 ml aliquots of ice-cold Buffer A. Specific binding was defined as the total [$^{125}$I-Tyr$^4$]bombesin bound in the presence of the test peptide minus that bound in the presence of 1 µM unlabeled GRP.

For BIM-26226, the IC$_{50}$ value (i.e., the concentration required to inhibit 50% of specific binding of [$^{125}$I-Tyr$^4$] bombesin) was calculated to be 0.50 nM. BIM-26226, thus, has a high affinity for the GRP receptor. In other words, it is a GRP ligand.

Determining the Antagonistic Activity of a GRP Ligand

A calcium mobilization assay can be utilized to screen for GRP ligands which possess antagonistic activity. A working example follows:

Rat AR42J cells were cultured in DMEM medium containing 10% fetal bovine serum (Sigma, St. Louis, Mo.) in an atmosphere of 5% $CO_2$ and 95% air at 37° C. After 5 days of culture, the cells were harvested by incubating in a 0.3% EDTA/phosphate buffered saline solution (Sigma, St. Louis, Mo.) (25° C.) and washed twice by centrifugation. The washed cells were resuspended in Hank's-buffered saline solution (HBSS) (Sigma, St. Louis, Mo.) for loading of the fluorescent $Ca^{2+}$ indicator Fura-2AM (Molecular Probes, Eugene, Oreg.). Cell suspensions of approximately $10^6$ cells/ml were incubated with 2 µM Fura-2AM for 30 min at 25° C. Unloaded Fura-2AM was removed by centrifugation (twice) in HBSS, and the final cell suspensions were transferred to a spectrofluorometer (Hitachi F-2000, Tokyo, Japan) equipped with a magnetic stirring mechanism and a temperature-regulated cuvette holder. After equilibration to 37° C., a test peptide or a known GRP antagonist was added for measurement of $Ca^{2+}$ mobilization. The excitation and emission wavelengths were 340 and 510 nm, respectively.

Bombesin (10 nM) was found to increase intracellular calcium concentration by 505 nM, while BIM-26226 (10 nM) had no effect on intracellular calcium levels. When pretreated with BIM-26226 (10 nM), bombesin (10 nM) only increased the intracellular calcium concentration by 300 nM, 205 nM less than when only bombesin was present. BIM-26226, thus, antagonized the calcium mobilization activity of bombesin.

Treating Pulmonary Hypertension with a Bombesin Antagonist

BIM-26226, a bombesin antagonist, was further administered to a male patient to test its efficacy in lowering the pulmonary systolic or diastolic pressure.

The patient, aged 43, complained of increasing shortness of breath under moderate exertion. He did not smoke, but did suffer from alcoholic liver disease. A clinical diagnosis of pulmonary hypertension, secondary to liver disease, was made. This diagnosis was subsequently confirmed with Swan-Ganz catheterization, which demonstrated a pulmonary pressure of 90/30 mm Hg (normal<20/5 mm Hg) in the patient. A chest radiograph showed marked prominence of pulmonary arteries and echocardiography tricuspid regurgitation and generally enlarged pulmonary arteries. His pulmonary function, blood gases, and liver function were all normal. Furthermore, serum estimations of the gut hormones GRP, vasointestinal peptide, pancreatic polypeptide, gastrin, glucagon, and neurotensin were also normal. A therapeutic trial of diltiazem, a calcium-channel antagonist, did not lower the pulmonary pressure.

An 8 G french introducer (Arrow, Reading, Pa.) was inserted into the right internal jugular vein of the patient. A 7 G french triple lumen-balloon inflation lumen Swan-Ganz line (Abbot, N. Chicago, Ill.) was inserted through the introducer. The catheter was first floated through the right atrium and ventricle into the pulmonary artery, and was then connected to a Hewlett Packard monitor (Model 66s, M1166A) using modules M1006A, M1020A, 1029A, 1008A, and M1166A. Measurements of central venous pressure, pulmonary artery pressure, mean pulmonary pressure, cardiac index, cardiac output, and pulmonary vascular resistance were analyzed directly. A 20 G arterial line was inserted into the left radial artery (Arrow, Reading, Pa.) for measurement of systemic blood pressure and blood gas partial pressure estimations.

The study was conducted in two phases. The placebo phase, which lasted 24 hours, consisted of an infusion of normal saline (0.9% NaCl) at a constant rate of 50 ml/hr. The active phase consisted of an infusion of BIM-26226 in increasing concentrations. BIM-26226 was supplied as lyophilized powder. BIM-26226 was reconstituted in water, and then diluted in normal saline initially to give an infusion concentration of 5 µg/kg/hr. The concentration was increased every four hours to a maximum of 200 mcg/kg/hr. BIM-26226 was administered through the jugular line at a constant infusion rate of 50 ml/hr. Observations as detailed above were recorded at least hourly, though more often if indicated. In addition, blood samples were taken every four hours for biochemical profile, hematological screening, and both peripheral and central GRP levels. The GRP level samples were collected on ice, centrifuged, and snap-frozen. Analysis on the GRP levels was performed using an established radioimmunoassay.

Other than a mild urticarial response during the early active phase, the patient had no adverse events to the bombesin antagonist.

FIG. 1 summarizes the study. The pulmonary systolic and diastolic pressures are compared between both the infusion of the saline placebo (Plac sys and Plac dias) and BIM-26226 (BIM sys and BIM dias). The doses of BIM-26226 administered and the administration scheme are shown at the top of FIG. 1, e.g., 5 µg/kg/hr four hours initially. Pulmonary systolic pressure (BIM sys) started to decrease at an infusion rate of 25 µg/kg/hr and declined further with increasing concentration of BIM-26226 from 90 mm Hg to 55 mm Hg at an infusion rate of 200 µg/kg/hr. Upon discontinuation of drug administration, the pulmonary pressure was seen to rise over a period of 15 min. (i.e., within two half-lives of the drug). Upon rechallenge with BIM-26226, the pulmonary systolic pressure again dramatically decreased. BIM-26226 slightly raised diastolic pressure (BIM dias) from 35 mm Hg to 42 mm Hg at an infusion rate of 200 µg/kg/hr.

Upon infusion of BIM-26226, no changes were seen in the cardiac output, cardiac index, right atrial pressure, systemic blood pressure, peripheral vascular resistance, or blood biochemistry.

Other Embodiments

The foregoing description has been limited to specific embodiments of the invention. It will be apparent, however, that variations and modifications may be made to the invention, with the attainment of some or all of the advantages of the invention. Such embodiments are also within the scope of the following claims.

What is claimed is:

1. A method of lowering the pulmonary systolic pressure of a subject suffering from pulmonary hypertension, said method comprising administering to the subject an amount of a bombesin antagonist, said amount being effective to lower the systolic pressure.

2. The method of claim 1, wherein said bombesin antagonist is administered parenterally.

3. The method of claim 2, wherein said bombesin antagonist is administered by implantation of a sustained release formulation.

4. The method of claim 3, wherein said bombesin antagonist is administered subcutaneously.

5. The method of claim 2, wherein said bombesin antagonist is administered by inhalation.

6. The method of claim 2, wherein said bombesin antagonist is administered intravenously.

7. The method of claim 6, wherein said bombesin antagonist is administered continuously.

8. The method of claim 1, wherein said subject is a human.

9. The method of claim 8, wherein said subject suffers from primary pulmonary hypertension.

10. The method of claim 9, wherein said bombesin antagonist is administered parenterally.

11. The method of claim 10, wherein said bombesin antagonist is administered by implantation of a sustained release formulation.

12. The method of claim 11, wherein said bombesin antagonist is administered subcutaneously.

13. The method of claim 10, wherein said bombesin antagonist is administered by inhalation.

14. The method of claim 10, wherein said bombesin antagonist is administered intravenously.

15. The method of claim 14, wherein said bombesin antagonist is administered continuously.

16. The method of claim 8, wherein said subject suffers from secondary pulmonary hypertension.

17. The method of claim 16, wherein said bombesin antagonist is administered parenterally.

18. The method of claim 17, wherein said bombesin antagonist is administered by implantation of a sustained release formulation.

19. The method of claim 18, wherein said bombesin antagonist is administered subcutaneously.

20. The method of claim 17, wherein said bombesin antagonist is administered by inhalation.

21. The method of claim 17, wherein said bombesin antagonist is administered intravenously.

22. The method of claim 21, wherein said bombesin antagonist is administered continuously.

* * * * *